United States Patent
Bloomfield et al.

(10) Patent No.: US 7,589,318 B2
(45) Date of Patent: Sep. 15, 2009

(54) MASS DEFECT TRIGGERED INFORMATION DEPENDENT ACQUISITION

(75) Inventors: Nic Bloomfield, Newmarket (CA); Yves LeBlanc, Toronto (CA)

(73) Assignees: MDS Inc., Concord, Ontario (CA); Applied Biosystems Inc., Framingham, MA (US)

( * ) Notice: Subject to any disclaimer, the term of this patent is extended or adjusted under 35 U.S.C. 154(b) by 213 days.

(21) Appl. No.: 11/620,061

(22) Filed: Jan. 5, 2007

(65) Prior Publication Data
US 2007/0164207 A1 Jul. 19, 2007

Related U.S. Application Data

(60) Provisional application No. 60/756,208, filed on Jan. 5, 2006.

(51) Int. Cl.
*B01D 59/44* (2006.01)
(52) U.S. Cl. .................. 250/282; 250/281; 250/287; 436/173
(58) Field of Classification Search ............... 250/282, 250/287, 283; 702/22, 23, 24, 26, 27, 28; 436/173
See application file for complete search history.

(56) References Cited

U.S. PATENT DOCUMENTS

| | | | | |
|---|---|---|---|---|
| 5,073,713 | A * | 12/1991 | Smith et al. | 250/282 |
| 6,958,473 | B2 * | 10/2005 | Belov et al. | 250/282 |
| 2005/0023454 | A1 | 2/2005 | Bateman et al. | |
| 2005/0098721 | A1 | 5/2005 | Bateman et al. | |
| 2005/0272168 | A1 * | 12/2005 | Zhang et al. | 436/173 |
| 2007/0023633 | A1 * | 2/2007 | Wang et al. | 250/282 |
| 2007/0038387 | A1 * | 2/2007 | Chen et al. | 702/23 |

OTHER PUBLICATIONS

Haiying Zhang et al., "JMS Letters", Journal of Mass Spectrometry, 2003; 38: 1110-1112, Published online in Wiley InterScience (www.interscience.wiley.com).
Mingshe Zhu et al., "Detection and Characterization of Metabolites in Biological Matrices Using Mass Defect Filtering of Liquid Chromatography/High Resolution Mass Spectrometry Data", DMD Fast Forward. Published on Jun. 30, 2006.
International Preliminary Report on Patentability. PCT App. No. PCT/CA2007/000010, dated Jul. 8, 2008.

* cited by examiner

*Primary Examiner*—David A Vanore
*Assistant Examiner*—Michael Maskell
(74) *Attorney, Agent, or Firm*—Bereskin & Parr LLP/S.E.N.C.R.L., s.r.l.

(57) ABSTRACT

Systems and methods for analyzing compounds in a sample. In one embodiment, a mass spectrometer includes an ion source for emitting a plurality of ions from a sample together with a detector positioned downstream of said ion source and configured to detect the impact of emitted ions on the detector. The mass spectrometer also includes a controller operatively coupled to the detector and to the ion source and configured to calculate the m/z for each detected ion. The controller comprises a mass defect filter configured to determine if the m/z for each detected ion falls within a predetermined mass defect range. The mass spectrometer also includes data storage coupled to the controller, wherein the data storage is configured to store detected ion m/z data corresponding to the m/z for a detected ion if the m/z falls within the mass defect range. The mass spectrometer may also include an ion mass filter positioned downstream of the ion source and operatively coupled to the controller. The ion mass filter is configured to selectively filter for ions substantially corresponding to the stored detected ion m/z data. The spectrometer may also include a fragmentor operatively coupled to the ion mass filter, wherein the fragmentor is configured to fragment each selected ion and to emit each fragment towards the detector. The controller is operatively coupled to the fragmentor and configured to calculated the m/z for each fragment detected by the detector. The data storage is preferably further configured to store fragment m/z data corresponding to the m/z for each detected fragment.

12 Claims, 8 Drawing Sheets

Regular IDA

| Metabolite Mass/amu | 418 | 402 |
|---|---|---|
| # of Found Metabolites | 3 | 3 |
| # of MS/MS recorded | 2 | 3 |
| Success Rate | 66 | 100 |

IDA with mass defect

| Metabolite Mass/amu | 418 | 402 |
|---|---|---|
| # of Found Metabolites | 4 | 4 |
| # of MS/MS recorded | 3 | 4 |
| Success Rate | 75 | 100 |

FIG. 4C

MASS DEFECT TRIGGERED INFORMATION DEPENDENT ACQUISITION

FIELD OF THE INVENTION

The present invention relates generally to the field of mass spectrometry.

BACKGROUND OF THE INVENTION

Mass spectrometers are used for producing mass spectrum of a sample to find its composition. This is normally achieved by ionizing the sample and separating ions of differing masses and recording their relative abundance by measuring intensities of ion flux. For example, with time-of-flight mass spectrometers, ions are pulsed to travel a predetermined flight path. The ions are then subsequently recorded by a detector. The amount of time that the ions take to reach the detector, the "time-of-flight", may be used to calculate the ion's mass to charge ratio, m/z.

Additional information (aside from precursor mass) on a given ion can then be obtained by fragmenting the ion via CID (collision induced dissociation) in a collision cell (or other mean) generate an MSMS spectrum. In most instrument with MSMS capabilities, the process of generating a mass spectrum, selecting an precursor ion and performing an MSMS (mass spectrum/mass spectrum) spectrum can be performed in an automated mode over and LC (liquid chromatography) analysis (or by infusion). This mode of acquisition is frequently referred to as Information Dependant Acquisition (IDA) or Data Dependant Experiment (DDE).

Often, samples to be analyzed include bodily fluids taken from test subjects such as animals in laboratories. As a result, the sample ions typically include both drug metabolites of interest, as well as irrelevant endogenous ions from the test subject. If the drug metabolites of interest are in low concentrations, creating a total ion chromatogram (TIC) of the sample ions may result in difficulties in identifying the drug metabolites. The ion flux or drug metabolites with low concentrations may be subsumed within the flux signals of the irrelevant endogenous ions.

The applicants have accordingly recognized a need for systems and methods for analyzing and identifying ions from samples.

SUMMARY OF THE INVENTION

In one aspect, the present invention is directed towards a method for analyzing compound in a sample. The method comprises the steps of:
(a) Determining a mass defect range;
(b) Emitting ions from the sample;
(c) Detecting the impact of the ions on a detector;
(d) Calculating the m/z for each detected ion;
(e) Determining if the m/z falls within the mass defect range; and
(f) Storing data corresponding to the m/z if the m/z falls within the mass defect range.

The method may also include the steps of:
(g) Selectively capturing at least one ion having a m/z which corresponds substantially to the stored m/z data; and
(h) Fragmenting the captured ion and determining the m/z of at least one fragment of the captured ion.

In another aspect, the invention is directed towards a mass spectrometer having a mass defect filter.

In yet a further aspect, the present invention is directed towards a mass spectrometer. The mass spectrometer includes an ion source for emitting a plurality of ions from a sample together with a detector positioned downstream of said ion source and configured to detect the impact of emitted ions on the detector. The mass spectrometer also includes a controller operatively coupled to the detector and to the ion source and configured to calculate the m/z for each detected ion. The controller comprises a mass defect filter configured to determine if the m/z for each detected ion falls within a pre-determined mass defect range. The mass spectrometer also includes data storage coupled to the controller, wherein the data storage is configured to store detected ion m/z data corresponding to the m/z for a detected ion if the m/z falls within the mass defect range. The mass spectrometer may also include an ion mass filter positioned downstream of the ion source and operatively coupled to the controller. The ion mass filter is configured to selectively filter for ions substantially corresponding to the stored detected ion m/z data. The spectrometer may also include a fragmentor operatively coupled to the ion mass filter, wherein the fragmentor is configured to fragment each selected ion and to emit each fragment towards the detector. The controller is operatively coupled to the fragmentor and configured to calculated the m/z for each fragment detected by the detector. The data storage is preferably further configured to store fragment m/z data corresponding to the m/z for each detected fragment.

BRIEF DESCRIPTION OF THE DRAWINGS

The present invention will now be described, by way of example only, with reference to the following drawings, in which like reference numerals refer to like parts and in which:

FIG. 4A-4E are printouts showing results of experiments contrasting regular IDA results and results obtained using the systems and methods of the present invention.

DETAILED DESCRIPTION OF THE INVENTION

Figure 1:
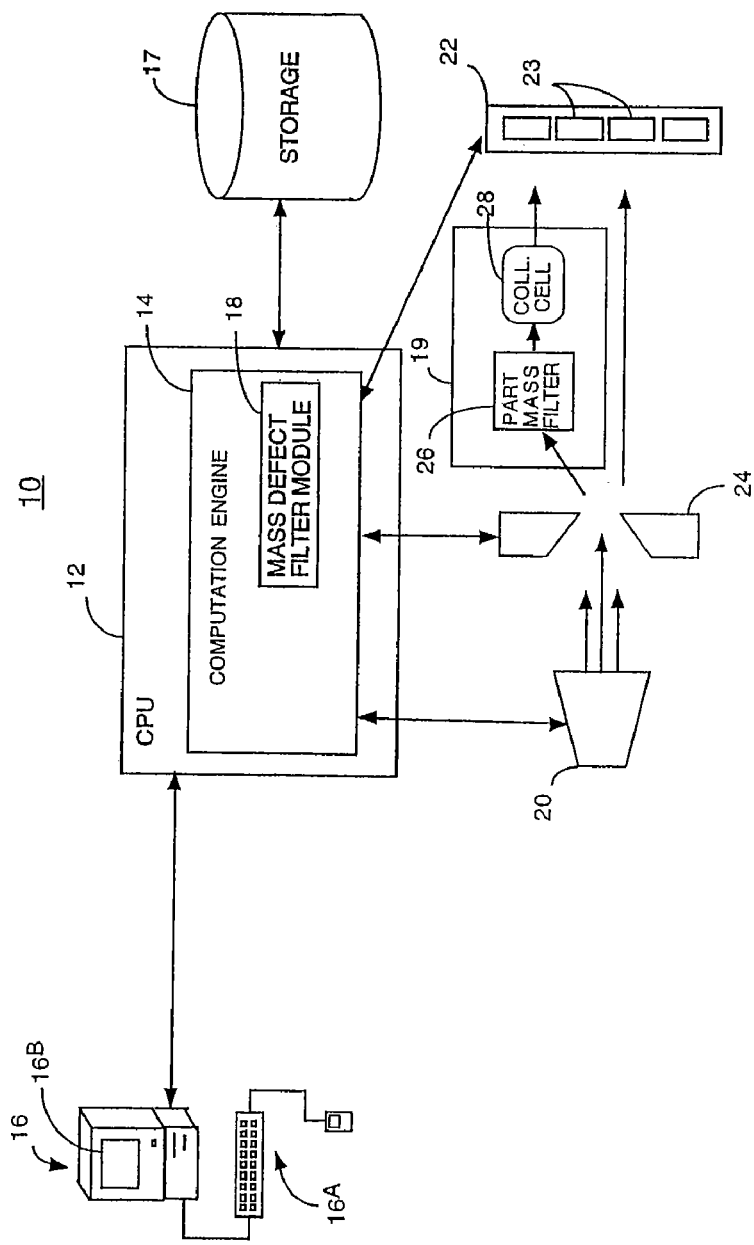
FIG. 1 is a schematic diagram of a mass spectrometer made in accordance with the present invention.

Referring to FIG. 1, illustrated therein is a mass spectrometer (which may be an MS/MS system such as a hybrid quadrupole time-of-flight such as the QSTAR XL LC/MS/MS System sold by Applied Biosystems/MDS SCIEX), referred to generally as 10, made in accordance with the present invention. The system 10 is preferably configured to be capable of performing information dependent acquisition (IDA) in accordance with the present invention, as will be understood.

The spectrometer 10 comprises a suitably programmed controller or central processing unit (CPU) 12 having a programmed ion flux computation engine 14. An input/output (I/O) device 16 (typically including an input component $16^A$ such as a keyboard or control buttons, and an output component such as a display $16^B$) is also operatively coupled to the CPU 12. Data storage 17 is also preferably provided. The CPU 12 will also include a mass defect filter module 18 (which may form part of the computation engine 14) configured for determining a mass defect range as will be discussed in greater detail, below. The spectrometer 10 will preferably also include a selection and fragmentation module 19.

The spectrometer 10 also includes an ion source 20, configured to emit ions, generated from the sample to be analyzed. As will be understood, the ions from the ion source 20 can be in the form of a continuous stream of ions; or the stream can be pulsed to generate a pulsed beam of ions; or the ion source 20 can be configured to generate a series of pulses in which a pulsed beam of ions is emitted.

Accordingly, the ion source 20 may be a continuous ion source, for example, such as an electron impact, chemical ionization, or field ionization ion sources (which may be used in conjunction with a gas chromatography source), or an electrospray or atmospheric pressure chemical ionization ion source (which may be used in conjunction with a liquid chromatography source), or a desorption electrospray ionization (DESI), or a laser desorption ionization source, as will be understood. A laser desorption ionization source, such as a matrix assisted laser desorption ionization (MALDI) can typically generate a series of pulses in which a pulsed beam of ions is emitted.

The ion source 20 can also be provided with an ion transmission ion guide, such as a multipole ion guide, ring guide, or an ion mass filter, such as a quadrupole mass filter, or an ion trapping device, as generally know in the art (not shown). For brevity, the term ion source 20 has been used to describe the components which generate ions from the compound, and to make available the analyte ions of interest for detection. Other types of ion sources 20 may also be used, such as a system having a tandem mass filter and ion trap.

A detector 22 (having a plurality of anodes or channels 23) is also provided, which can be positioned downstream of the ion source 20, in the path of the emitted ions. Optics 24 or other focusing elements, such as an electrostatic lens can also be disposed in the path of the emitted ions, between the ion source 20 and the detector 22, for focusing the ions onto the detector 22.

The selection and fragmentation module 19 is also typically positioned between the ion source 20 and the detector 22. The module 19 typically includes an ion mass filter 26 (which is operatively coupled to the CPU 12), together with a fragmentor 28 such as a collision cell (capable of fragmenting ions) operatively coupled to the filter 26. As will be understood, the fragmentor 28 may comprise fragmentation technologies in which an ion is selected to perform MSMS to generate fragment information including but not limited to Resonance Excitation (inside linear trap). As will also be understood, in operation, the filter 26 and optics 24 may be controlled by the controller 12 to selectively regulate the flow of emitted ions.

Figure 2:
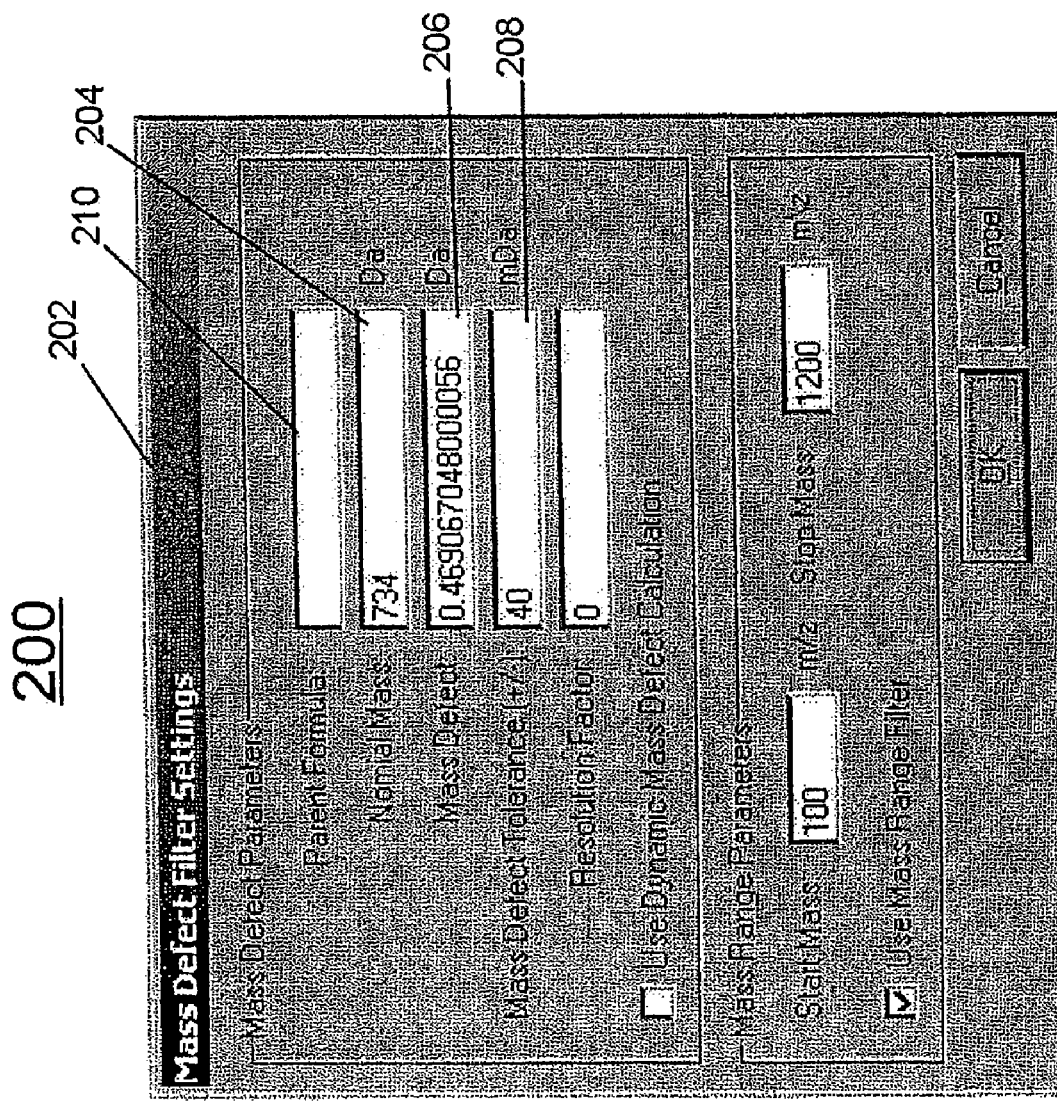
FIG. 2 is a screen shot of an I/O device of the mass spectrometer of FIG. 1.

Referring now to FIG. 2, illustrated therein is a screenshot 200 of a computer screen 202 as may be displayed on display 16$^B$.

Figure 3:
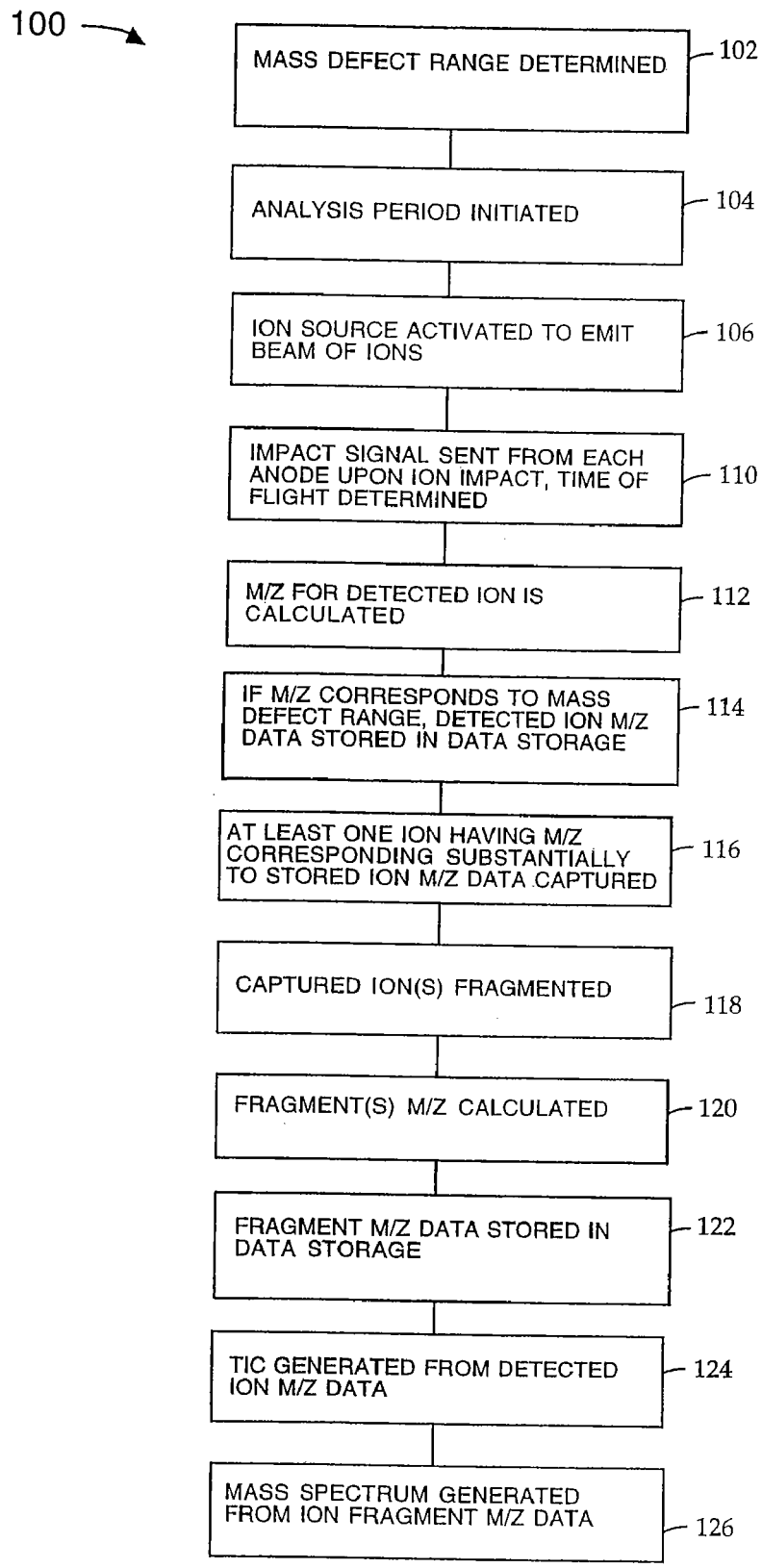
FIG. 3 is a flow diagram illustrating the steps of a method of analyzing a compound in accordance with the present invention.

FIG. 3 sets out the steps of the method, referred to generally as 100, carried out by the spectrometer system 10 during an analysis period. Typically, before the analysis period is commenced, a mass defect range is determined (Block 102). Generally the mass defect range may be determined through two different approaches.

A first approach to determining a mass defect range involves the user directly inputting to the computation engine 14 a nominal mass value and mass defect value together with a tolerance range through the I/O device 16 (such as via fields 204, 206 & 208 on screen 202). A tolerance range of +/−20 mDa is often preferred, but other ranges are possible (including +/−50 mDa and greater) as will be understood. It should be understood that multiple mass defect ranges may be determined by the computation engine 14 in order to cover multiple analytes.

A second approach to entering a mass defect range involves the inputting to the computation engine 14 by the user of the chemical formula of the compound being researched (such as via field 210 on screen 202). The computation engine 14 is preferably programmed to calculate the nominal mass value of inputted chemical formulas. Alternatively, the nominal mass and defect value of many chemical formulas may be previously calculated and stored as a library of data in the data storage 17, and simply indexed and retrieved by the computation engine 14. In yet another alternative approach, if the mass defect is specified relative to molecular weight using a linear equation, then the computation engine 14 is programmed to calculate the mass defect range at run time based on the ions' molecular weight as will be understood—this method of calculating a mass defect range will more typically be used for analysis involving peptides. In each approach, the user manually inputs the tolerance range (via field 206).

The user will then typically input a command to commence an analysis period (typically via the I/O device), upon receipt of which the computation engine 14 is programmed to initiate the first stage of the analysis period (Block 104). When the first stage of an analysis period is commenced, a beam of ions from the sample compound is emitted from the ion source 20 (Block 106). As will be understood, the sample compound may include a drug and its associated metabolites and/or peptides for analysis.

During every pulse, each time one or more ions impact with an anode 23, an impact signal is sent from the anode 23 which is received by the engine 14, and the engine 14 also determines travel time data corresponding to the travel time or "time of flight" for the detected ion (Block 110). The computation engine 14 is programmed to calculate the m/z for each detected ion corresponding to the determined travel time data (Block 112). The engine 14 then compares the calculated m/z and compares it to the mass defect range determined in Block 102.

If the centroid or the decimal portion of the m/z falls within the mass defect range, for the purposes herein the m/z of the detected ion will be considered to "correspond to" or "fall within" (or wording to similar effect) the mass defect range, and the engine 14 will then store in data storage 17 m/z data corresponding to the calculated m/z (Block 114). As will be understood, in this step the engine 14 may perform the filtration and selection process "on the fly" and only store m/z data corresponding to the calculated m/z falling within the mass defect range, or alternatively the engine may store more or all m/z data during the first stage of the analysis period and then filter the m/z data and store a separate listing of only m/z data which falls within the mass defect range.

Typically, once the first stage of the analysis period is completed, the system 10 then commences the second stage of the analysis period (which may be referred to as the "MS/MS stage") and selectively captures at least one ion having a m/z which corresponds substantially to the stored m/z data (Block 116). To accomplish this, the controller 12 typically configures the filter 26 and/or the optics 24 to selectively filter the stream of emitted ions for ions having a m/z which corresponds substantially to the stored m/z data (which may include one or more m/z data, preferably for peaks, falling within the mass defect range).

Ions having a m/z corresponding substantially to the stored m/z data are captured within the collision cell 28. The captured ions are then fragmented (Block 118).

In a manner similar to that described in relation to Blocks 110 to 112, the ion fragments are then emitted towards the detector 22 and the m/z of one or more of the detected ion fragments is calculated (Block 120), and m/z data corresponding to the calculated m/z of such ion fragments is stored in the data storage 17 (Block 122).

As will be understood, the controller 12 may generate a TIC (total ion chromatogram) or mass spectrum that consists of ions having their centroid within the mass defect range (forming peaks) from the m/z data stored in the data storage 17 (Block 124). The controller 12 may also generate a mass spectrum for the ion fragments based on the ion fragment m/z data stored in the data storage 17 (Block 126).

Figure 4A:
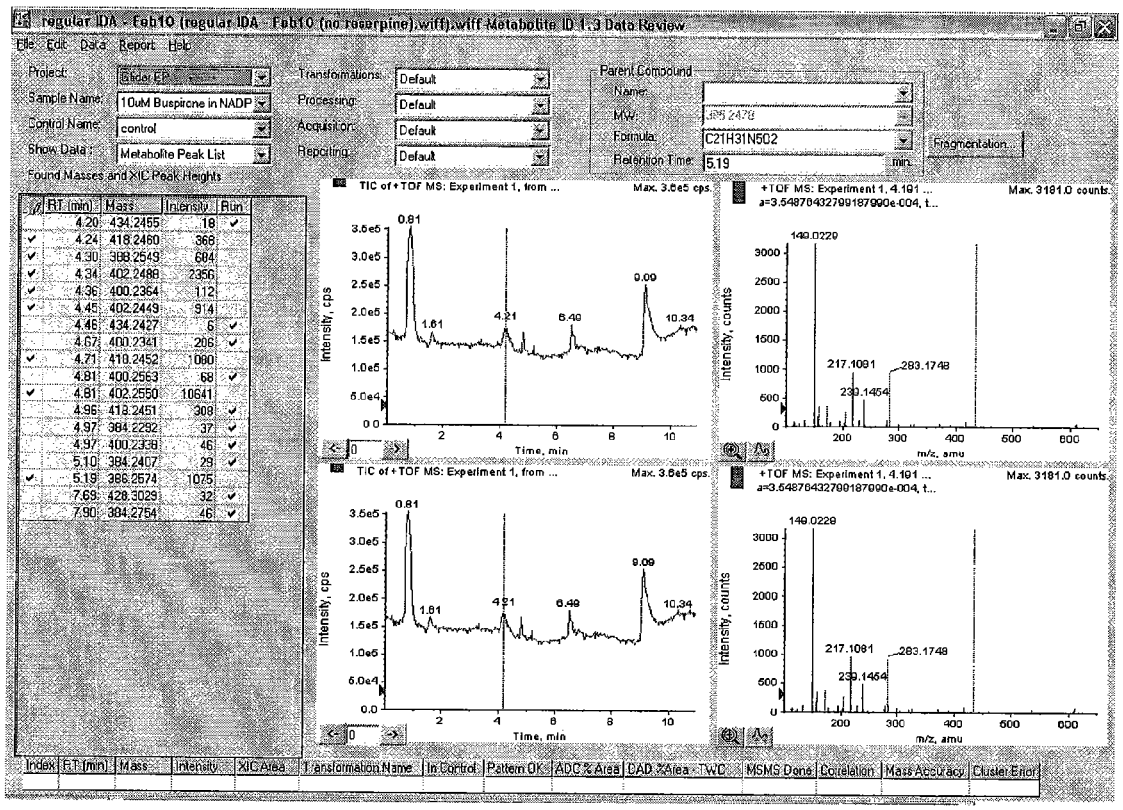
Figure 4B:
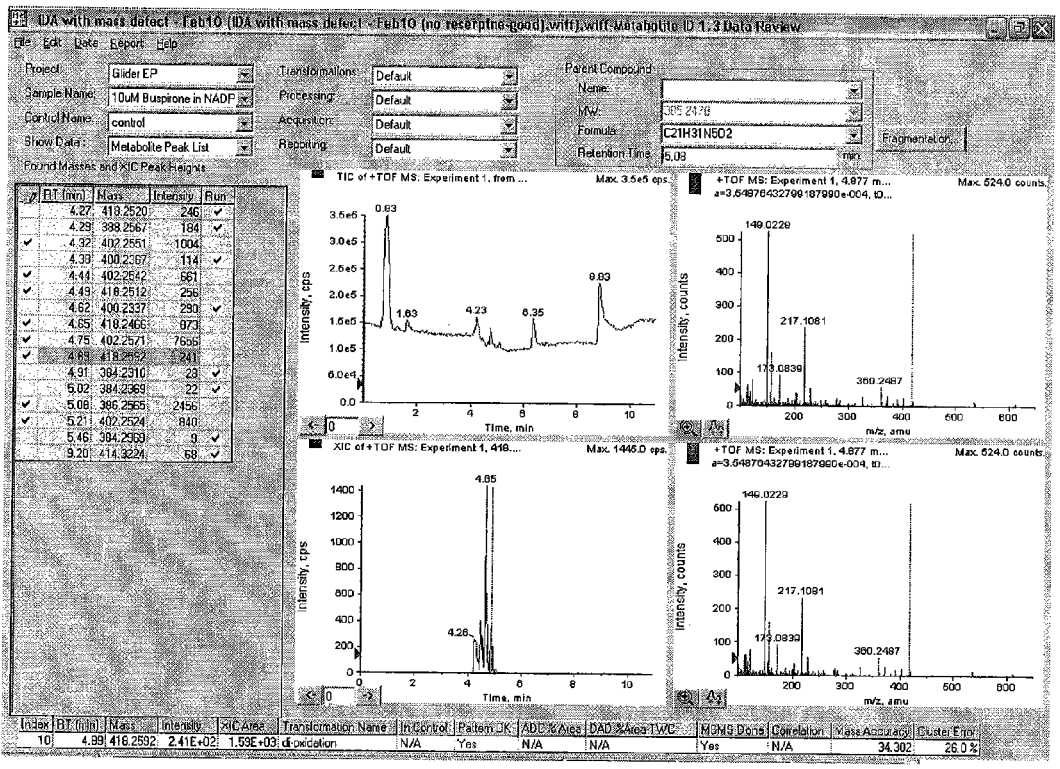

Referring now to FIG. 4A, illustrated therein are the results of an experiment analyzing a compound containing buspirone metabolites using regular IDA. These results may be contrasted with the results shown in FIG. 4B of an experiment analyzing the same compound used in the experiment of FIG. 4A containing buspirone metabolites, but using the IDA methods 100 and systems 10 of the present invention. FIG. 4C compares the results of FIGS. 4A and 4B and notes improved results and success rates for finding and recording metabolites using the system and methods of the present invention as contrasted with "regular IDA".

Figure 4D:
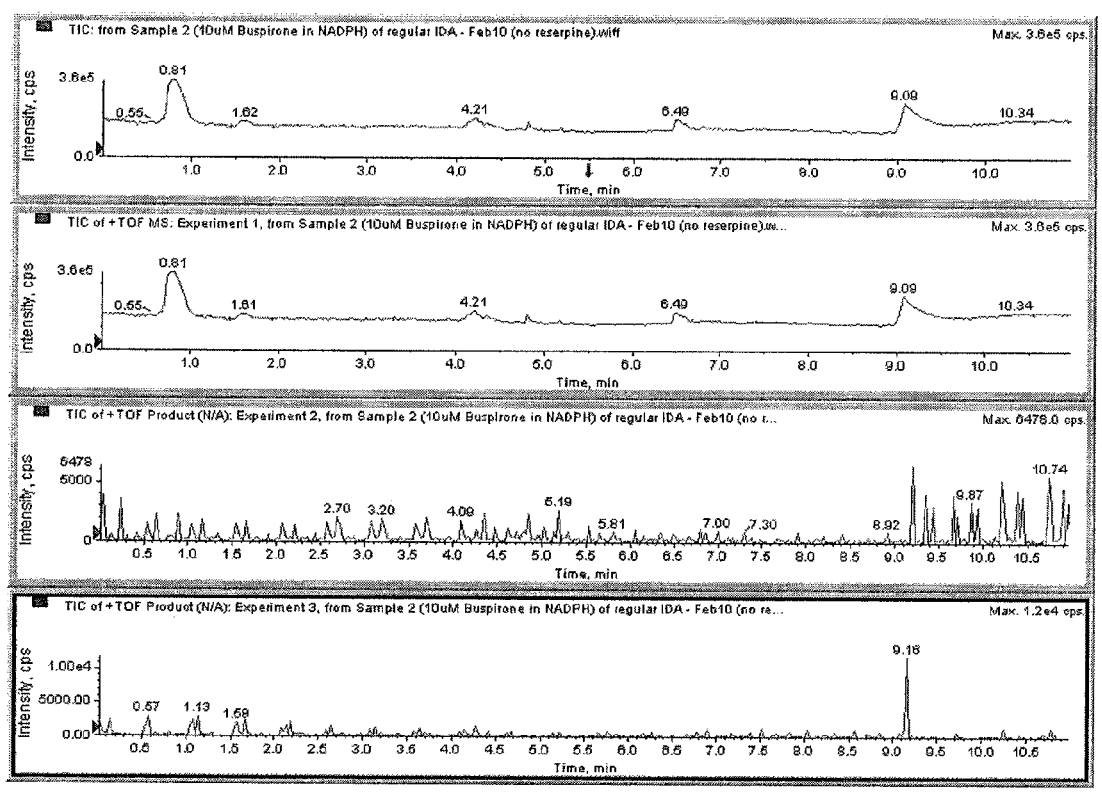
Figure 4E:
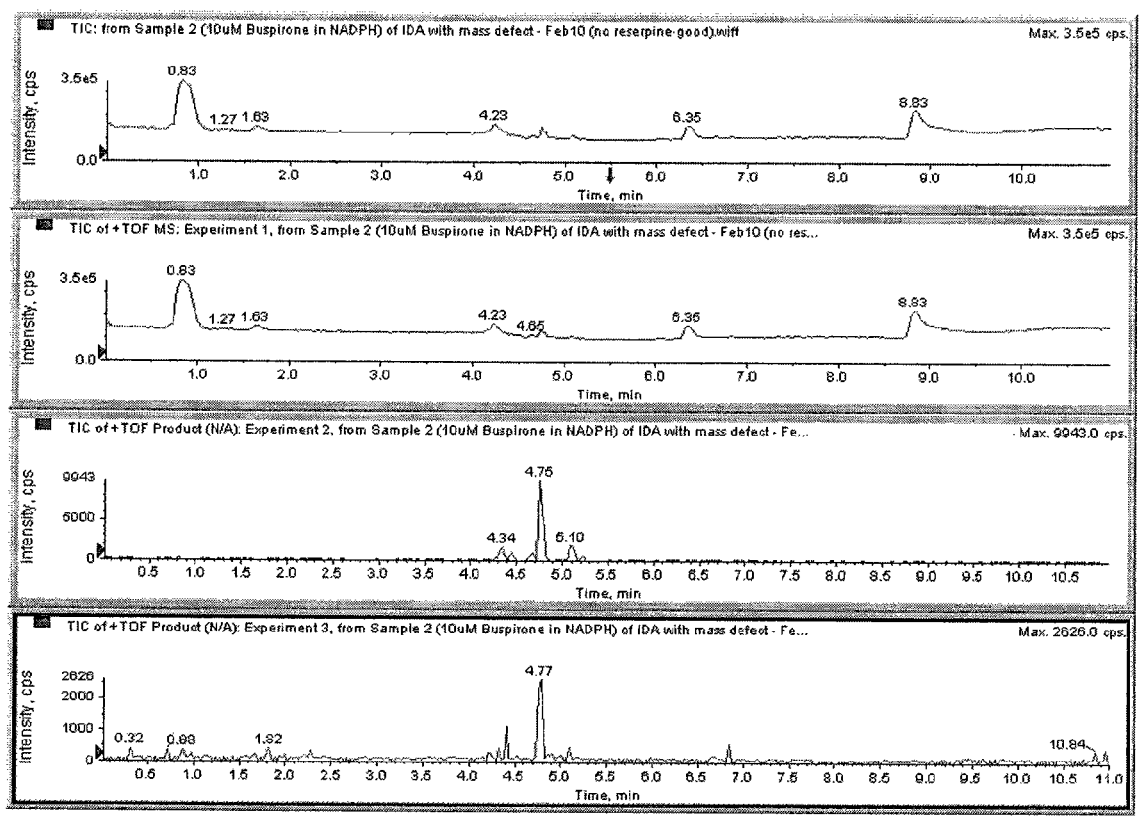

FIG. 4D illustrates a TIC view of regular IDA performed on a sample compound containing buspirone metabolites. It is noted that the MS/MS TIC does not clearly identify the metabolites. FIG. 4E illustrates a TIC view of IDA performed using the systems and methods of the present invention on the same sample compound used in the experiment of FIG. 4D, containing buspirone metabolites. It is noted that the MS/MS TIC clearly identifies the metabolites and resembles an XIC of buspirone and its metabolites as will be understood.

Thus, while what is shown and described herein constitute preferred embodiments of the subject invention, it should be understood that various changes can be made without departing from the subject invention, the scope of which is defined in the appended claims.

The invention claimed is:

1. A method for analyzing compounds in a sample, comprising the steps of:
   (a) Determining a mass defect range;
   (b) Emitting ions in a stream from the sample;
   (c) Detecting the impact of the ions on a detector;
   (d) Calculating the m/z for each detected ion;
   (e) Determining if the m/z falls within the mass defect range; and
   (f) Storing data corresponding to the m/z if the m/z falls within the mass defect range; and
   (g) Selectively capturing at least one ion having a m/z which corresponds substantially to the stored m/z data, wherein the selectively capturing comprises selectively filtering the stream of emitted ions for ions having a m/z which corresponds substantially to the stored m/z data.

2. The method as claimed in claim 1, further comprising the step of:
   (h) Fragmenting the at least one captured ion and determining the m/z of at least one fragment of the at least one captured ion.

3. The method as claimed in claim 2, further comprising the step of:
   (i) Storing ion fragment m/z data corresponding to the m/z of the at least one fragment.

4. The method as claimed in claim 3, further comprising the step of:
   (j) generating a mass spectrum corresponding to the ion fragment m/z data.

5. A mass spectrometer comprising:
   (a) an ion source for emitting a stream of ions from a sample;
   (b) a detector positioned downstream of said ion source and configured to detect the impact of emitted ions on the detector;
   (c) a controller operatively coupled to the detector and to the ion source and configured to calculate the m/z for each detected ion;
   (d) wherein the controller comprises a mass defect filter configured to determine if the m/z for each detected ion falls within a pre-determined mass defect range;
   (e) data storage coupled to the controller, wherein the data storage is configured to store detected ion m/z data corresponding to the m/z for a detected ion if the m/z falls within the mass defect range; and
   (f) a selection and fragmentation module positioned downstream of said ion source and operatively coupled to the controller, wherein said selection and fragmentation module is configured to selectively capture at least one ion from the stream having a m/z which corresponds substantially to the stored detected ion m/z data.

6. The mass spectrometer as claimed in claim 5, wherein said fragmentation module is configured to fragment each selected ion and to emit each fragment towards said detector.

7. The mass spectrometer as claimed in claim 5, wherein the selection and fragmentation module comprises:
   (i) an ion mass filter positioned downstream of said ion source and operatively coupled to the controller, wherein the ion mass filter is configured to selectively filter the stream for ions substantially corresponding to the stored detected ion m/z data.

8. A mass spectrometer as claimed in claim 7, wherein the selection and fragmentation module comprises:
   (ii) a fragmentor operatively coupled to the ion mass filter, wherein the fragmentor is configured to fragment each selected ion and to emit each fragment to said detector.

9. A mass spectrometer as claimed in claim 8, wherein the controller is operatively coupled to the fragmentor and configured to calculated the m/z for each fragment detected by the detector.

10. The mass spectrometer as claimed in claim 9, wherein the data storage is further configured to store fragment m/z data corresponding to the m/z for each detected fragment.

11. The mass spectrometer as claimed in claim 8, wherein the fragmentor comprises a collision cell.

12. The mass spectrometer as claimed in claim 8, wherein the fragmentor comprises resonance excitation.

* * * * *